(12) United States Patent
Miller (10) Patent No.: US 9,670,504 B2
(45) Date of Patent: Jun. 6, 2017

(54) TRANSGENIC SYSTEM FOR REVERSIBLY IMMORTALIZING MAMMALIAN QUIESCENT CELLS

(75) Inventor: Alain Miller, Mons (BE)

(73) Assignee: CILBIOTECH S.A., Mons (BE)

( * ) Notice: Subject to any disclaimer, the term of this patent is extended or adjusted under 35 U.S.C. 154(b) by 240 days.

(21) Appl. No.: 14/124,184

(22) PCT Filed: Jul. 6, 2012

(86) PCT No.: PCT/EP2012/063310
§ 371 (c)(1),
(2), (4) Date: Dec. 5, 2013

(87) PCT Pub. No.: WO2013/007656
PCT Pub. Date: Jan. 17, 2013

(65) Prior Publication Data
US 2014/0199766 A1    Jul. 17, 2014

(30) Foreign Application Priority Data
Jul. 8, 2011    (EP) .................................... 11173193

(51) Int. Cl.
C12N 15/85    (2006.01)
(52) U.S. Cl.
CPC .......... *C12N 15/85* (2013.01); *C12N 2510/04* (2013.01)
(58) Field of Classification Search
CPC ............................ C12N 15/85; C12N 2510/04
See application file for complete search history.

(56) References Cited

U.S. PATENT DOCUMENTS

2002/0142393 A1    10/2002    Baiker et al.
2004/0053876 A1*    3/2004    Turner .................... C07H 21/02
                                                                514/44 A
2004/0115776 A1    6/2004    Simesen et al.

FOREIGN PATENT DOCUMENTS

WO    WO 2008/036262 A2    3/2008
WO    WO 2010/000491 A1    1/2010
WO    WO 2010/049777 A1    5/2010

OTHER PUBLICATIONS

Ehrhardt et al. "Optimization of Cis-Acting Elements for Gene Expression from Nonviral Vectors In Vivo." Hum Gene Ther. Feb. 10, 2003;14(3):215-25.*
Freundlieb et al. "A tetracycline controlled activation/repression system with increased potential for gene transfer into mammalian cells." J Gene Med Jan.-Feb. 1999;1(1):4-12.*

International Search Report and Written Opinion of the International Searching Authority for International Application No. PCT/EP2012/063310, mailed on Sep. 26, 2012.
Argyros et al., "Persistent episomal transgene expression in liver following delivery of a scaffold/matrix attachment region containing non-viral vector," *Gene Therapy*, vol. 15(24), pp. 1593-1605 (Dec. 1, 2008).
Argyros et al., "Development of S/MAR minicircles for enhanced and persistent transgene expression in the mouse liver," *Journal of Molecular Medicine*, vol. 89(5), pp. 515-529 (May 1, 2011).
Chang et al., "Comparison of early passage, senescent and hTERT immortalized endothelial cells," *J Biotechnol.*, vol. 151(3), pp. 231-241 (Dec. 15, 2010).
Girod et al., "Genome-wide prediction of matrix attachment regions that increase gene expression in mammalian cells," *Nature Methods*, vol. 4(9), pp. 747-753 (Sep. 1, 2007).
Haga et al., "Efficient immortalization of primary human cells by p16 INK4a-specific short hairpin RNA or Bmi-1, combined with introduction of hTERT," *Cancer Science*, vol. 98(2), pp. 147-154 (Feb. 2007).
Salmon et al., "Reversible Immortalization of Human Primary Cells by Lentivector-Mediated Transfer of Specific Genes," *Molecular Therapy*, vol. 2(4), pp. 404-414 (Oct. 2000).
Sgourou et al., "Physiological levels of HBB transgene expression from S/MAR element-based replicating episomal vectors," *Journal of Biotechnology*, vol. 143, pp. 85-94 (2009).
Teixeira et al., "An efficient gene transfer system for hematopoietic cell line using transient and stable vectors," *Journal of Biotechnology*, vol. 88, pp. 159-165 (2001).
Wong et al., "Non-viral S/MAR vectors replicate episomally in vivo when provided with a selective advantage," *Gene Therapy*, vol. 18(1), pp. 82-87 (Jan. 1, 2011) (Abstract).
Wong et al., "Genetic Modification of Cancer Cells Using Non-Viral, Episomal S/MAR Vectors for In Vivo Tumour Modelling," *Molecular Therapy*, vol. 20, Suppl. 1, p. S235 (May 2012).
Wu et al., "Reversible immortalization of rat pancreatic [beta] cells with a novel immortalizing and tamoxifen-mediated self-recombination tricistronic vector," *Journal of Biotechnology*, vol. 151(3), pp. 231-241 (Feb. 1, 2011).

* cited by examiner

*Primary Examiner* — Titilayo Moloye
(74) *Attorney, Agent, or Firm* — Knobbe, Martens, Olson & Bear LLP (57) ABSTRACT

A transgene for endowing human quiescent cells from primary cultures with exogenously inducible telomere length homeostasis and cell cycle traverse is described. The transgene includes at least three promoter sequences; a G1-specific RNA interference sequence which is operably linked downstream of a first promoter sequence; a telomere length maintenance gene sequence which is operably linked downstream to a second promoter sequence; a Scaffold/Matrix attachment region (S/MAR) element positioned downstream in frame with said telomere length maintenance gene sequence and an exogenously-inducible transcriptional regulation system. The transgene is useful to immortalize human quiescent cells from primary cultures.

13 Claims, 4 Drawing Sheets

TRANSGENIC SYSTEM FOR REVERSIBLY IMMORTALIZING MAMMALIAN QUIESCENT CELLS

CROSS-REFERENCE TO RELATED APPLICATIONS

This application is the U.S. National Phase under 35 U.S.C. §371 of International Application PCT/EP2012/063310, filed Jul. 6, 2012, which claims priority to EP 11173193.1, filed Jul. 8, 2011.

TECHNICAL FIELD

The invention pertains to the technical field of generating reversibly immortalized cells or cell lines starting from cells derived from primary cultures ("primary cells") which are situated in the so-called "replication senescent" state as a result of them being accumulated somewhere in the G1 phase of the cell cycle. In particular, the invention relates to a transgene which encodes a telomere length maintenance gene and a short hairpin loop RNA (shRNA) to prevent the translation of a cell-specific G1-acting tumour suppressor messenger RNA, both activities together culminating in the immortalization of the primary cells. The vector furthermore comprises a Scaffold/Matrix Attachment Region (S/MAR) whose transcription-in frame with that of the inducible telomere length maintenance gene ensures replication of the transgene in phase with the host cell genome. In a further aspect, the present invention relates to a method to reversibly immortalize a primary human cell by incorporation of the transgene of the invention into the target cell.

BACKGROUND

Many fundamental studies on primary human tissues are hampered by the paucity of obtainable substrates. Even though cell-based therapy holds great promises for the treatment of a number of hereditary as well as acquired disorders, it will mostly remain a theoretical prospect unless the requirements for providing a high number of therapeutic cells can be met. As compared to the controlled expansion of human embryonic-induced pluripotent (progenitor) stem cells, with their concomitant risks of potential tumourigenic outcomes, the expansion represents an attractive alternative for producing large quantities of cells for either experimental or therapeutic purposes.

In the most desirable scenario, cells harvested in vivo are induced to grow indefinitely in vitro, a process referred to as immortalization. Furthermore, the primary phenotype and physiological activity of the cells, including their non-dividing status if relevant, can be restored at will. Cell lines therefore obtained can be expanded, extensively characterized both in their immortalized and "de-immortalized" (i.e., after removal/silencing of the telomere length maintenance genes) states. They can be used for analyses that range from basic physiology to proteomics (of low-abundance proteins), for the production of specific proteins, toxicity testing, drug-drug interactions, drug discovery and, in selected cases, for transplantation (personalized medicine).

As most primary cells do not grow indefinitely in culture, there is need for methods to reversibly immortalize primary cells and to overcome the eventual senescent state of these cells. After a series of population doublings, the number of which varies by species, cell type, culture conditions, cells that enter a replication senescent state will no longer divide. This state makes it that normal human cells exhibit a limited replicative lifespan. The latter is characterized by the progressive intracellular accumulation of one or another of a series of tumour suppressor proteins which inhibit G1 cyclin-dependent kinases to phosphorylate p53 and pRb, two transcription regulation proteins.

Prolonged exit from the cell cycle and arrest in G1 is marked by distinct changes in cell morphology, appearance of pycnotic granules, progressive vacuolisation, alterations in gene expression and decreased telomere length which eventually lead to cell death.

Some primary cells become spontaneously immortalized and escape replication senescence. Most of the time, they have genetic mutations which makes them less a reliable representative of their starting tissue's phenotype.

Another mechanism that is used to momentarily overcome senescence is the inhibition of telomere shortening. Telomeres are repetitive "TTAGGG" stretches of DNA at the very end of the linear chromosomes. Their specific conformation avoids the chromosome being recognized as a break and protects the ends from exonuclease degradation and telomeres fusions. Telomerase Reverse Transcriptase (TERT) will lengthen the telomeres by de novo synthesis of telomeric repeats ensuring telomere length homeostasis. Ectopic expression of the human TERT (hTERT) gene has been used to induce momentary immortalization in some primary cells. However, many lines of evidence suggest that activation of the telomerase is not sufficient for immortalization of most cell types and immortalization must in such cases be achieved by introduction of viral genes such as the SV40 large T antigen. Salmon et al. (2000) describe a lentiviral approach to induce immortalization in senescent cells by introducing both hTERT and SV40 in the cell (Salmon et al., 2000, Mol. Ther., (4):404-414). However, even though introduction of viral genes such as the Epstein Barr Virus (EBV), Simian virus 40 (SV40), large T antigen (Tag), Adenovirus E1A and E1B, human papilloma virus (HPV) E6 and E7 have been equally used to permanently immortalize primary cells, such immortalized cells lose the properties of primary cells by inactivating one or another (depending on the cell type) of the above mentioned tumour suppressor genes, which allow cells to re-enter the cell cycle and permanently bypass replicative senescence. CHO, human Hela and PER-C6 cells are examples of such established cell lines.

It has also been shown that under routine cell culture conditions, many primary cells progressively increase their intracellular levels of a tumour suppressor leading to their exit from the cell cycle and accumulation somewhere in G1. In some cell types, tumour suppressor proteins appear to be a key requirement for efficient immortalization by hTERT. This suggests that immortalization of human primary cells should be achievable through the concomitant ectopic expression of hTERT and depletion of the cognate tumour suppressor protein.

Haga et al. (2006) have described the immortalization of primary cells by ectopically introduction of an hTERT enzyme and simultaneously repressing $p16^{INK4A}$ by a $p16^{INK4A}$ shRNA and introduction of Bmi-1 (Haga et al., 2007, Cancer Science, 98:147-154). Therefore, retroviral vectors were cloned and introduced in the cell by means of retroviral transfection. The authors found that cells which simultaneously repress p16 and express hTERT were able to become permanently immortalized.

WO 2 010 000 491 discloses an inducible method and one or more transgenes to induce either immortalization or senescence in primary cells, by introducing at least one immortalizing gene sequence and one sequence to downregulate a tumour suppressive gene. The cassettes are introduced by a lentiviral system, which introduces the transgenes into the genome of the host cell at random sites.

The conventional vectors currently used in the process of primary cell immortalization rely either on random integration in the host genome or are only transiently retained.

There remains a need in the art for an improved method of inducing immortalization in primary cells. Both create serious problems with respect to safety, reproducibility and efficiency. Random integration may lead to insertional mutagenesis and to silencing of the transgene. Transient expression, on the other hand, implies that repeated treatments would be necessary and this in most cases is not desirable. Therefore the ideal vector should be retained in many cells without integration. A number of virus-based vectors replicate episomally in some mammalian cells. However, since replication of these constructs relies on the presence of virus-encoded trans-acting factors, which often lead to cell transformation, their use for genetic manipulation of eukaryotic cells is largely limited.

Therefore, there is a need for an alternative method to induce immortalization in primary cells, which preferentially has a low immunogenicity, which is devoid of the risk of random insertional mutagenesis (retroviruses) and epigenetic silencing of the introduced vector or transgene. Furthermore, it is desirable that the vectors carrying the shRNA and hTERT cassettes be maintained in both dividing and non-dividing cells. Finally, the method should equally allow for the reversibility of the state of the cells, that is, it should be possible to reverse the state of a cell, immortalized by the present invention, to its initial state, that is its primary quiescent fully differentiated state.

The invention thereto aims to provide a method for immortalizing human primary cells in a controlled and stable manner. The invention therefore discloses a transgenic system comprising one or more transgenes which can be obtained in large amounts by prior amplification in bacteria, which comprises cassettes that upon exogenous induction will activate telomere length homeostasis and cell cycle traverse i.e. immortalization of the primary host cell. The transgenic system is designed in such a way that it remains episomal and will not integrate in the host genome. This will avoid the risk of random insertional mutagenesis and its consequences. Furthermore, the designed transgenic system is not dependent on viral components for its replication in the host cell, therefore eliminating the potential risk of cell transformation. The present invention furthermore provides for a mechanism whereby the state of the immortalized cells can be reversed to its original replication senescent state without altering the genetic and phenotypic background of the primary cell.

SUMMARY OF THE INVENTION

In a first aspect, the invention provides for a transgenic system to be used for immortalizing quiescent cells, comprising at least one transgene, whereby the transgenic system comprises:
a) at least three promoter sequences;
b) an G1-acting cell-specific RNA interference sequence (shRNA) which is operably linked downstream of a first promoter sequence;
c) a telomere length maintenance gene sequence which is operably linked downstream to a second promoter sequence;
d) a Scaffold/Matrix Attachment region (S/MAR) element positioned downstream in frame with said telomere length maintenance gene sequence and;
e) an exogenously-inducible transcriptional regulation system.

In a second aspect, the present invention provides a method to immortalize quiescent cells from primary cultures, comprising the steps of:
a) providing the quiescent cells from primary cultures;
b) introducing the transgenic system according to the claims 1 to 8 into the human quiescent cells; whereby the said transgenic system replicates in phase with the host cell genome without integrating;
c) adding an inducing agent to the growth medium of said cells;
d) overexpressing the telomere length maintenance gene present in the said transgenic system;
e) preventing the expression of a G1-acting cell specific tumour-suppressor protein by a specific RNA interference sequence present in the said transgenic system.

In a further aspect, the present invention provides for the immortalized cell which is obtained by the method as described here above, and whereby its immortalized status can be irrevocably reversed to its replication senescent starting stage at a well-defined moment by depletion of the said inducer agent.

DESCRIPTION OF FIGURES

FIG. 4 depicts a schematic overview of an exemplary embodiment of the transgenic system according to the present invention, containing two transgenes, whereby one transgene, the "control transgene" comprises the components of the control region (1), meaning the transactivator and transsilencer genes with corresponding constitutive promoter sequences. In this particular example, the used transactivator is rtTA$_2$$^s$-M2, while the transsilencer is tTS. The second transgene, the "regulation transgene" bears the components of the regulation region (2), comprising the telomere length maintenance gene TERT and the RNA interference directed against a G1-tumour suppressor messenger RNA (mRNA), in this case against p16$^{INK4a}$ mRNA. Both transgenes will furthermore each bear a different S/MAR element in order to maintain their replication in phase with the genome of the host cell positioned in frame, downstream of the said control region and of the said telomere length maintenance gene (Girod, P. A. et al., 2007, Nature Methods 4: 747-753; Liebich at al., 2001: 372-374).

DETAILED DESCRIPTION OF THE INVENTION

The present invention provides for a transgenic system and method to obtain immortalized primary cells. A primary cell may become, preferentially reversibly, immortalized by introducing a transgenic system in the said primary cells which is able to replicate autonomously and episomally. The transgenic system can be as long as required maintained in the said host cell. When presence of said expressed transgenic system is no longer wanted or needed, mechanisms are provided to eliminate the said transgenic system in a few cell division rounds, without a reminiscence of the presence of said transgenic system. Thus, the said once immortalized human primary cell returns to its original quiescent state.

Unless otherwise defined, all terms used in disclosing the invention, including technical and scientific terms, have the meaning as commonly understood by one of ordinary skilled in the art to which this invention belongs. By means of further guidance, term definitions are included to better appreciate the teaching of the present invention.

As used herein, the following terms have the following meanings:

The term "transgene" refers to DNA or RNA vehicle, such as a plasmid, a minicircle or a composite of both structures, which optionally may comprise nucleotide sequences enabling replication of the DNA or RNA in a suitable host cell, such as a bacterial host for amplification purpose, and which can be introduced in a eukaryotic host cell. In this invention, the transgene includes genes which are transcribed into mRNA and eventually translated (except for S/MAR) into proteins when the sequence is expressed in the genetically modified target cell.

The term "transgenic system" refers to the sum of the transgenes that are introduced in the host cell by standard transfection means.

"Transfection" refers to the introduction of an exogenous nucleotide sequence, such as DNA vectors in the case of mammalian target cells, into a target cell whether or not any coding sequences are ultimately expressed. Numerous methods of transfection are known to those skilled in the art, such as: chemical methods (e.g., calcium-phosphate transfection), physical methods (e.g., electroporation, microinjection, particle bombardment), fusion (e.g., liposomes), receptor-mediated endocytosis (e.g., DNA-protein complexes, viral envelope/capsid-DNA complexes) and by biological infection by viruses such as recombinant viruses (Wolff, J. A., ed, Gene Therapeutics, Birkhauser, Boston, USA (1994)). Genetic modification of the target cell is the indicia of successful transfection. In this case, extended numbers of population doublings is the indicia of successful transfections.

The term "immortalized" refers to a cell wherein all safeguard mechanisms restricting proliferation like, e.g. p53 and pRB, telomere shortening are inactivated. A cell is termed immortal when it proliferates indefinitely. An immortalized cell line is therefore a cell line capable of indefinite proliferation and hence is expandable without limitation. Importantly, immortal cells are not necessarily transformed cells meaning that immortal cells do not necessarily have a tumour phenotype.

The term "primary cells" includes: cells present in a tissue, organ, or a part thereof, removed from an organism; cells present in a suspension of cells obtained from said tissue, organ, or part thereof; cells present in an explanted tissue; cells of said suspension or said explant when for the first time plated; and cells present in a suspension of cells derived from the first time plated cells.

The term "cell line" refers to a population of cells capable of continuous growth and division in-vitro under appropriate conditions.

"Episomal" refers to a unit of genetic material, such as a vector, an expression vector or a transgene which is able to replicate independently without the need to integrate in the genome of the host cell. The said unit of genetic material exists in parallel with the genome of the host cell and is replicated during the cell cycle whereby in the course of this the unit of genetic material is copied, depending on the number of copies present before and after cell division and whereby the said replicated units of genetic material are distributed statistically in the resulting cells.

"Non-viral" vector, expression vector or transgene relates to the fact that the vector, expression vector or transgene is devoid of any viral sequences which may contribute in the autonomous replication of the transgene in the host genome and that the delivery of the said vector, expression vector or transgene into the targeted host cell occurs without the aid of (recombinant) viruses as delivery vehicle.

A "minicircle" is generally derived from a parental maxi-plasmid which is produced in large quantities in a bacterial system. The origin of replication and an antibiotic resistant gene of prokaryotic origin, required for amplification of the maxi-plasmid are surrounded by target F sites for excision by FLP recombinase. To eliminate potential epigenetic manifestations (gene silencing), all material of bacterial origin is generally eliminated following treatment of the maxi-plasmid with the enzyme Flp recombinase to yield a mixture of covalently closed circular supercoiled DNA molecules (maxi-plasmid, mini-plasmid comprising the prokaryotic elements and the sought after minicircle), from which the minicircle is then isolated and purified. In absence of proven epigenetic effect, the prokaryotic part can be kept to avoid tedious and cumbersome treatment with the recombinase enzyme and the ensuing minicircle purifications. Compared to plasmids, minicircles generally benefit from higher transfection efficiencies and longer ectopic expression. Still this class of episomes reveals intrinsic instability and integration after several months of continuous culture. In the meantime, minicircles exhibit a replication pattern which is coupled to that of the host cell in which it replicates once per cell cycle in synchrony with the host genome.

The term "origin of replication" (ORI) is understood as meaning the general starting point or origin of replication in eukaryotic and prokaryotic cells, as well as viruses.

These ORIs support the replication and form the attachment points for various replicators.

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

One aspect of the current invention provides for a transgenic system used to endow human quiescent cells from primary cultures with exogenously induced telomere length maintenance and cell cycle traverse commonly referred to as "immortalization".

The said transgenic system comprises at least one transgene, which on its turn comprises one or more gene sequences and/or genetic units under the control of one or more inducible promoter sequences which cooperate or play a role in inducing immortalization (extended life span and cell cycle re-entry/traverse) in human quiescent cells from primary cultures when introduced in host cells.

The transgenic system is divided in a "control region" (1) and a "regulation region" (2), whereby the said regulation region (2) comprises the genes and/or genetic units that actually play a role in inducing immortalization in quiescent cells, and whereby the said control region (1) comprises genes that control the expression of said genes and/or genetic units of the regulation region.

In one embodiment, the said control region (1) and regulation region (2) will be both combined on one transgene of said transgenic system. In another embodiment, the said control region and regulation region are positioned on separate transgenes of the transgenic system.

In a preferred embodiment, the said gene sequences encode for genes that are known to play a role in the immortalization process of a cell, namely telomere length homeostasis and cell cycle re-entry/traverse. In a most preferred embodiment, the said telomere length maintenance gene is TERT which encodes for the telomerase reverse transcriptase catalytic subunit. In a most preferred embodiment, said TERT is rat TERT, the rat telomerase reverse transcriptase catalytic subunit. In most cells, telomeres become progressively shorter as the cell multiplies. After a certain number of cell divisions, the telomeres become so short that they trigger the cell to stop dividing or to undergo apoptosis. Telomerase counteracts the shortening of telomeres by adding small repeated segments of DNA to the ends of chromosomes each time the cell divides, ensuring telomere length homeostasis.

In one embodiment, the said telomere length maintenance gene is placed under control of a constitutive promoter region. In another, more preferred embodiment, the said promoter sequence controlling the expression of the said telomere length maintenance gene is exogenously inducible.

In a further aspect, the said genetic units inducing immortalization of a cell comprise techniques able to downregulate the translation of a tumour suppressor gene known to play a role in senescence of cells. Said techniques encompass the use of RNA interference molecules directed against one or more tumour suppressor mRNA. The method of using siRNA and miRNA is well known in the art, e.g. as described by Pei and Tusschl, 2006 (Nat. methods. 3: 670-676 and Chang et al., 2006, Nat. Methods. 3: 707-714.) In a preferred embodiment, the said genetic units inducing immortalization comprise a shRNA directed to said tumour suppressor mRNA. In a preferred embodiment, the said shRNA are directed against a G1-specific tumour suppressor mRNA. In a most preferred embodiment, the said shRNA's are directed against a G1-specific tumour suppressor mRNA chosen from the group of $p16^{INK4A}$, $p15^{INK4B}$, $p18^{INK4C}$, $p19^{INK4D}$, $p21^{Cip1}$, $p27^{Kip1}$, or $p27^{Kip2}$ mRNA's.

In one embodiment, the said telomere length maintenance gene is placed under control of a constitutive promoter region. In another, more preferred embodiment, the said promoter sequence controlling the expression of the said telomere length maintenance gene is inducible.

In order to achieve immortalization either the telomere length maintenance TERT gene or the downregulation of G1-specific tumour suppressor mRNAs can be applied. But the immortalization process can also be induced through a combination of a telomere length maintenance gene and the downregulation of tumour suppressor mRNA(s). For the human system it has been recognized by the present inventor that the presence of at least one telomere length maintenance gene is necessary as well as the downregulation of at least one G1-specific tumour suppressor gene to allow the generation of a succesfully immortalized primary cell.

In a most preferred embodiment, the said regulation region (2) of the transgenic system comprises at least one telomere length maintenance gene and at least one sequence which induces the depletion of a specific G1-tumour suppressor messenger RNA.

In a further aspect, the control region (1) of said transgenic system comprises a transcriptional regulation system, comprising transcriptional transactivator $rtTA_2^s$-M2 and transsilencer tTS which are able to interact with the said inducible promoter sequences situated in the regulation region (2). In a preferred embodiment, the said transsilencing and transactivator genes are each placed under the control of a constitutive promoter sequence. In another embodiment, transcription of said transsilencing and transactivator genes are controlled by one single constitutive promoter sequence and will result in a bicistronic transcript. An internal ribosome entry site (IRES) placed between said two genes will allow for translation initiation at a well-defined place of the mRNA and eventually provide for two separate proteins.

This transcriptional regulation system can be controlled externally by the presence or absence of an inducing agent to the medium of the cells. The said transcriptional transactivator and -silencer exert their effect on the inducible promoter sequences present on the said transgene. Upon absence of the said inducing agent, the said transcriptional transsilencer will interact with the said inducible promoters present in said regulation region, thereby preventing any activity of said promoter sequences.

However, upon presence of the said inducing agent, it is the inverse situation which prevails which results in transcription of the sequences controlled by said inducible promoter.

In a further alternative embodiment, provided the target primary cells manifest furin activity—as is usually the case with cells from the endocrine system—the IRES sequence is replaced by a nucleotide sequence corresponding to the consensus RAK/KRR furin cleaving site also providing two separate proteins. The transcriptional regulation system in the regulation region can be tightly controlled externally by the presence or absence of an inducing agent added to the growth medium of the cells. The said transcriptional transsilencing tS and transcriptional transactivator rtTA$_2^s$--M2 proteins exert their effect on the inducible promoters present in the regulation region on the said transgene. Upon absence of said inducing agent, the said transcriptional transsilencer tTS will interact with the said inducible P$_{Tight/U6}$ and P$_{Tet-T6}$ promoters in said regulation region thereby preventing any activity of said promoter sequences. However, upon presence of said inducing agent, the said inducing agent will allow the said transcriptional transactivator rtTA$_2^s$-M2 to bind to the said inducible P$_{Tight/U6}$ and P$_{Tet-T6}$ promoters, allowing activation of the latter two promoters, which results in transcription of the sequences controlled by said P$_{Tight/U6}$ and P$_{Tet-T6}$ promoters by RNA polymerase type III and II respectively.

In a preferred embodiment, the said transcriptional regulation system is a TET-ON/TET-OFF regulation system and the said inducing agent is an antibiotic more preferably tetracycline or doxycycline. The required concentration of the said inducing agent ranges from 300 up to 2000 ng per ml culture medium.

In yet another aspect of the present invention, the said transgenic system comprises at least one Scaffold/Matrix Attachment Region (S/MAR) element. S/MARs are typically 70% A/T-rich sequences and are often found in association with chromosomal origins of replication. Furthermore, they play a crucial role in maintaining chromosome structure and functioning in the eukaryotic nucleus. Most of the vectors or transgenes used in the immortalization of primary cells and which replicate episomally in eukaryotic cells are viral-based, such as for instance SV40-based vectors. The replication origins contained in these vectors require the interaction with virally encoded trans-acting factors. These proteins very often lead to permanent transformation of the transfected cells. For example the replication of SV40 DNA requires a single viral protein, the large T-antigen, whereas the other factors are supplied by the host cell. Infection with SV40 or transfection with vectors carrying the gene coding for the SV40 large T-antigen can lead to immortalization of primary cells and can induce tumour formation in animals. Therefore, such vectors are only partially useful for immortalization of primary cells. It is the aim of the current invention to provide for an episomal transgenic system to be used for the immortalization of primary cells which does not express any viral protein and thus avoids cell transformation. It was shown that S/MAR-based vectors can promote episomal replication and maintenance in mammalian cells (e.g. Piechaczek et al., 1999, Nuc. Acids Res.; Hagedorn et al., 2011, Hum. Gene Therapy). US 2 002 014 239 3 provides for an episomal replicating vector which comprises an S/MAR element. However, the vector still comprises an origin of replication (ORI) derived from SV40. The current invention provides for a transgenic system comprising at least one transgene which is able to replicate episomally by the presence of an S/MAR element and which is completely non-viral as it is devoid of a viral ORI.

In one embodiment, the said S/MAR element is under the control of a constitutive promoter sequence. In yet another embodiment, the said promoter sequence controlling the S/MAR element is inducible. Preferentially, in the said regulation region (2) of the transgenic system, the said S/MAR element is positioned downstream, in frame with the said telomere length maintenance gene sequence and is controlled by the same promoter sequence as the said telomere length maintenance gene sequence. Upon activation of the said inducible promoter sequence by the presence of said inducing agent, the S/MAR element will be readily transcribed and the said transgene will be replicated in phase with the host cell genome without any impact on the cell's differentiation. However, when transcription of the S/MAR is interrupted, the transgene will be lost from the host cell, without any integration. Regulation of transcriptional activity can therefore be applied to support or terminate the retention of said transgene. In the current invention, and when made use of an inducible promoter sequence, this can for instance be established by depletion of said inducing agent. In application where it is not desirable to terminate the replication of said transgene, the said S/MAR element may be controlled by a constitutive promoter sequence.

In one embodiment of the current invention, the said transgene of the transgenic system is a minicircle and lacks any residual elements for propagation in bacteria. A minicircle is generally produced from a parental maxiplasmid, which is capable of replicating in prokaryotic systems such as E. coli bacteria. The prokaryotic region in this so-called parental maxiplasmid usually contains recombination sites which flank the sequences of the said minicircle, an endonuclease restriction site for the destruction of the remaining parental plasmid and of the resulting miniplasmid after excision and a selection gene. In short, expression of said enzyme genes is induced, which results firstly in excision of the minicircle from the parental maxiplasmid and secondly will result in enzymatic degradation of the said parental maxiplasmid's and miniplasmid's backbone. In a subsequent step, the minicircle is purified through a CsCl density gradient. Apart from the fact that minicircles are devoid of any elements which support prokaryotic propagation, are self-replicating and non-viral, they furthermore have the advantage that they maintain a constant high level of gene expression over a significant period of time.

In another embodiment of the current invention, the inventor tried to overcome the cumbersome and labour-intensive production of minicircles by keeping a prokaryotic origin of replication in said minicircle, which allows the replication and amplification of the minicircle in bacteria. Additionally, the minicircle may be provided with an antibiotic-independent selection element, none of those elements influencing (epigenetic silencing) the eukaryotic part of the maxiplasmid.

To ensure stability of the transgenic system in the host cell, the transgene of said transgenic system should not exceed the size of 7 to 8 Kilo-base pairs (Kb). Furthermore, to prevent the risk of integration of said transgene in the host genome, the transgene should not be smaller than 3 Kb. Preferably the transgene should comprise a size between 4 Kb to 7 Kb.

As mentioned, the transgenic system according to the current invention comprises at least one transgene. In one embodiment, the host cell will receive a transgenic system with only one transgene (see FIG. 1), comprising the two components of the said control region (1), such as the transcriptional transactivator, the transsilencer and their corresponding common promoter sequence, such as for instance the constitutive EF1α promoter, as well as of the regulation region (2), with the telomere length maintenance gene, the S/MAR region and the shRNA interference directed against a G1-tumour suppressor mRNA. In another preferred embodiment, the host cell will receive a transgenic system with more than one transgene (see FIG. 4), whereby each said transgene comprises units which can, provided that they are all present in the same host cell, induce immortalization. This can for instance occur when the size of a single transgene exceeds the preferred size, hence risking instability of said transgene. Preferably, the host cell will receive two transgenes, with one transgene comprising only the components of the said control region, e.g. the transcriptional transactivator and transcriptional transsilencer with promoter sequence, while the other transgene comprises only the components of the said regulation region, comprising the telomere length maintenance gene and the shRNA sequence directed against a G1-tumour suppressor mRNA. Both transgenes will furthermore each bear an S/MAR element in order to maintain their replication in phase with the genome of the host cell. To prevent the risk of two identical S/MAR elements competing for the same location, the S/MAR elements of each transgene should be different.

Overall, the transgenic system comprising at least one transgene is preferably capable of transfecting cells and stably expressing gene sequences and/or genetic elements to enable growth of the cells for an extended period of time in vitro.

On a further subject, the current invention provides for a method to immortalize quiescent cells, preferentially of human origin, from primary cultures, comprising the steps of:
 a) providing the quiescent cells from primary cultures;
 b) introducing the transgenic system according to the claims 1 to 8 into the human quiescent cells; whereby the said transgenic system replicates in phase with the host cell genome without integrating;
 c) adding an inducing agent to the growth medium of said cells;
 d) overexpressing the telomere length maintenance gene present in the said transgenic system;
 e) preventing the translation of a G1-specific tumour-suppressor mRNA by a specific RNA interference sequence present in the said transgenic system.

The present invention is preferably directed to genetically modifying eukaryotic cells that are quiescent and otherwise incapable of extended growth in vitro. The latter eukaryotic cells are preferably derived preferably from human, mouse, rat, guinea pig, hamster, rabbit, chicken, cat, dog, a non-human primate, pig, sheep, cow, horse, fish, reptile, or amphibian origin. More preferably, the said primary cells are from human origin.

Introduction of the said transgenic system comprising the transgene(s) occurs through transfection. Transfection is understood as meaning the inclusion of the transgene in the cell. In a preferred embodiment, the said transfection occurs through lipofection, whereby small complexes are prepared comprising both the DNA and cationic lipids.

The negatively charged DNA binds spontaneously to the positively charged liposomes, forming DNA-cationic lipid reagent complexes.

Lipofection is well known in the prior art and comprises the use of cationic lipids which basic structure consists of a positively charged head group and one or two hydrocarbon chains. The charged head group governs the interaction between the lipid and the phosphate backbone of the nucleic acid, and facilitates DNA condensation. Often cationic lipids are formulated with a neutral co-lipid or helper lipid, followed by extrusion or microfluidization, which results in a unilamellar liposomal structure with a positive surface charge when formulated in water.

The positive surface charge of the liposomes also mediates the interaction of the nucleic acid and the cell membrane, allowing for fusion of the liposome/nucleic acid ("transfection complex") with the negatively charged cell membrane. The transfection complex is thought to enter the cell through endocytosis. Endocytosis is the process where a localized region of the cellular membrane uptakes the DNA: liposome complex by forming a membrane bound/intracellular vesicle. Once inside the cell, the complex must escape the endosomal pathway, diffuse through the cytoplasm, and enter the nucleus for gene expression. Cationic lipids are thought to facilitate transfection during the early steps of the process by mediating DNA condensation and DNA/cellular interactions.

Said transfection preferably occurs on adherent cells in a two-dimensional culture. In one embodiment, the cells might prior to transfection be subjected to a treatment with butyric acid, a known inhibitor of histone deacetylase.

The method according to the current invention makes use of said inducing agent which is provided to the medium of the said primary cells at a concentration range of 300 to 2000 ng per ml growth medium. The said inducing agent preferentially comprises an antibiotic, more preferentially tetracycline or Doxycyline.

In one embodiment of the invention, the expression of said RNA interference sequence of the system is dependent on the presence of the said inducing agent.

In another embodiment of the invention, the expression of said telomere length maintenance gene is dependent on the presence of the said inducing agent.

In a most preferred embodiment, both the expression of said RNA interference sequence and said telomere length maintenance gene are dependent on the presence of said inducing agent.

In another embodiment of the present invention, transcription of the said S/MAR element is dependent on the presence of the said inducing agent. Under these circumstances, absence of the said inducing agent will lead to loss of the S/MAR element in said host cell, hence eventually leading to entire loss of said transgene from the host cell. Therefore, the state of the immortalized primary will be reversed to its exact initial state and eventually go into senescence, without the presence of any exogenously introduced genetic material. As such, the cells become identical to their state before transfection.

In another embodiment, the transcription of said S/MAR element operably linked downstream of the telomere length maintenance gene (TERT) is constitutive, whereby the said immortalized primary cell will stay immortalized provided the G1-specific tumour suppressor mRNA is depleted, and whereby the presence of the said transgene bearing the transgenic system will be maintained in the host cell, independent of the presence of said inducing agent.

In a final aspect, the invention furthermore provides for a primary cell which has been immortalized through the method of the invention as described here above and whereby the said immortalized cell can irrevocably be reversed to its original state. This can occur at a well-defined moment, decided by the practitioner or researcher, by simply depleting the cells of said inducing agent. This can for instance occur by replacing the medium of the cells comprising the said inducing agent, by medium that is devoid of any traces of the said inducing agent. Absence of the said inducing agent, will lead to the loss of said transgene within 2 to 3 cell cycle replications.

The invention is further described by the following non-limiting examples which further illustrate the invention, and are not intended to, nor should they be interpreted to, limit the scope of the invention.

EXAMPLES

Example 1

Figure 1:
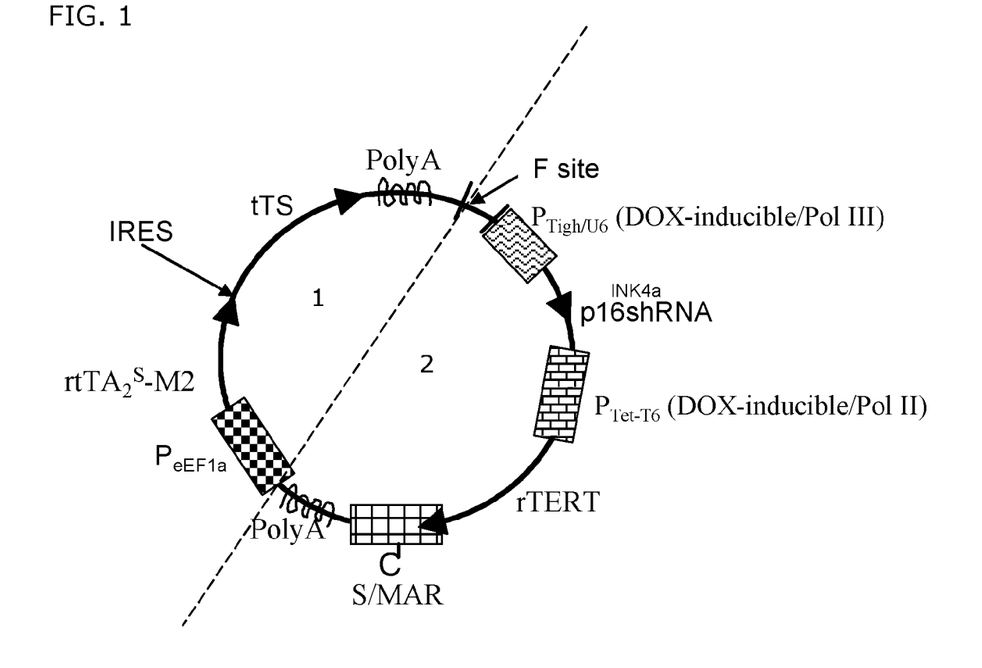
FIG. 1 depicts a schematic overview of an exemplary transgenic system according to the present invention, containing only one transgene, whereby said TERT and shRNA immortalizing sequences, as well as an S/MAR element are placed under control of doxycycline-inducible promoter sequences. The F site is a remnant following exposure to the enzyme Flp recombinase of the bacterial region surrounded by F-sites.

FIG. 1 depicts an exemplary embodiment of the transgenic system according to the current invention, comprising only one transgene, whereby said transgene is a minicircle, and is devoid of a prokaryotic region. The transgenic system according to FIG. 1 comprises a Tet-on/Tet-off system in the control region (1) with the transcriptional transactivator rtTA$_2^s$-M2 and the transcriptional transsilencer tTS constitutively expressed by use of the EF1α promoter. In this particular example, the said transcriptional transactivator and transcriptional transsilencer are transcribed as bicistronic mRNA and comprise an IRES in between which regulates translation. In another embodiment of the invention (not depicted), a second constitutive promoter may be provided which controls either the transcriptional transactivator or transcriptional transsilencer and whereby the presence of the IRES is dispensable. The transgenic system according to FIG. 1 comprises in the regulation region (2) rTERT as said telomere length maintenance gene, which will ensure telomere length homeostasis and a shRNA directed against the tumour suppressor mRNA p16$^{INK4a}$. Degradation of p16$^{INK4a}$ mRNA by such an RNA interference mechanism will lead to decreased intracellular levels of the p16$^{INK4a}$ protein and the activation of the cognate G1-specific cyclin-dependent kinase complex. Both immortalizing sequences are placed under control of inducible promoter sequences, susceptible to the presence or absence of doxycycline or tetracycline in the medium of the cells. The S/MAR element is equally put under control of said one of the inducible promoters. The F site present in the transgene according to FIG. 1 is a remnant, following exposure to the enzyme Flp recombinase, of the "floxed" bacterial region (region flanked by unidirectionally F sites) used to amplify the minicircle in bacteria. Mode of action of the said minicircle according to FIG. 1 occurs as follows:

- P$_{Tet-ON}$ (in presence of doxycycline): rtTA$^s$2-M2 binds P$_{Tight/U6}$ situated upstream of the shRNA cassette allowing RNA polymerase III (which preferentially transcribes short DNA sequences such as the small nuclear U6 RNA involved in splicing) to actively transcribe the shRNA and P$_{Tet-T6}$ so as to transcribe the TERT-S/MAR cassette via RNA plolymerase II. The transcriptional silencer tTS even present in large amounts does not influence the above effects.
- P$_{Tet-OFF}$ (in absence of doxycycline): rtTA$^s$2-M2 no longer binds P$_{Tight/U6}$ nor P$_{Tet-T6}$. The transcriptional silencer tTS is now capable to interact with both P$_{Tight/U6}$ and P$_{Tet-T6}$. Both shRNA and TERT-S/MAR cassettes are silenced. S/MAR being no longer transcribed makes the minicircle to be lost within two-three cell replication cycles.

The transgenic system as depicted in FIG. 1, when transfected in primary cells, ensures the immortalization of said primary cells. This allows providing an unlimited supply of differentiated, adult cells by urging them to re-enter the cell cycle. As widespread application of primary cells (for instance β pancreatic islet cells, hepatocytes, etc. . . . ) for the regeneration of tissues, organs and the treatment of diseases as diverse as insulin-dependent diabetes, diseases affecting the liver (fibrosis, fulminant hepatitis) and their sequelae (obesity, atherosclerosis, etc. . . . ), is dependent upon the availability of an unlimited supply of cells exhibiting the appropriate differentiated phenotype, the current invention provides for a method to readily produce large quantities of any given primary cells. Furthermore, upon reaching the required number of cells withdrawal of the said inducing agent makes it that the expression cassettes in the transgene are silenced and the complete transgene subsequently rapidly eliminated.

The choice of said tumour suppressor protein that should be depleted in order to obtain immortalized primary cells, depends on the origin of the primary cell, and should be carefully chosen. In general, the said tumour suppressor is chosen from the group of p15$^{INK4B}$, p16$^{INK4A}$, p18$^{INK4C}$, p19$^{INK4D}$, p21$^{Cip1}$, p27$^{Kip1}$, or p57$^{Kip2}$, all of them cyclin-dependent kinases which block the cells somewhere in G1. Table 1 shows the types of human primary cells and the related tumour suppressors that need to be downregulated in order to induce immortalization, next to the presence of a telomere length maintenance gene such as rTERT. It also shows that cells from an established cell line (Hela cells grow continuously) can be blocked somewhere in G1 following lovastatin-mediated activation of the tumour suppressor p27$^{Kip1}$.

TABLE 1

Types of Tumour Suppressors (cyclin-dependent kinase inhibitors) and related cells.

| Cell Type | Tumour suppressor/status |
|---|---|
| Epithelial (bronchial, mammal prostate, small airways) | p16$^{INK4a}$ |
| Dermal (keratinocytes, papille mesenchymal stem cells) | |
| Keratinocytes | p16$^{INK4a}$ |
| Human pancreatic β islet cells | p16$^{INK4a}$ |
| Human B Lymphocytes | p18$^{INK4c}$ |
| Human Hepatocytes | p15$^{INK4b}$ |
| Fibroblasts | p27$^{Kip1}$ |
| Human bladder carcinoma (Lovastatin) | p21$^{Cip}$ |
| Hela cells (Lovastatin) | p27$^{Kip1}$ (Syn p28-lovastatin) |
| Human osteoblasts | p27$^{Kip1}$ |
| Human osteoarthitic chondrocytes | p16$^{INK4a}$ |

Example 2

Figure 2:
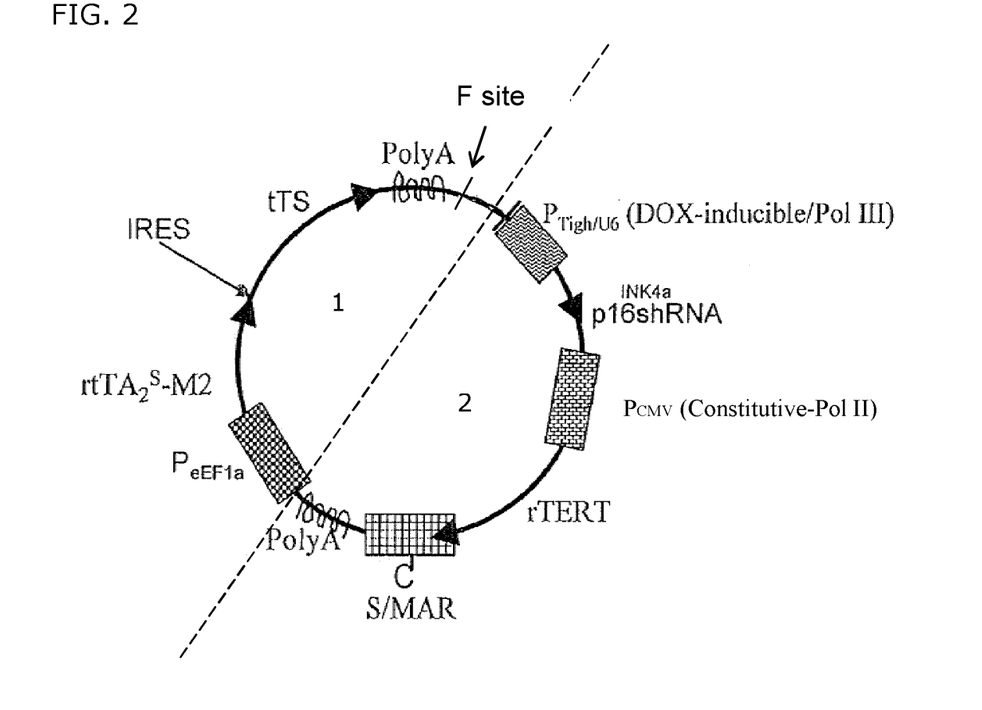
FIG. 2 depicts a schematic overview of an alternative embodiment of the transgenic system according to the present invention, containing only one transgene, whereby the said TERT telomere length maintenance gene positioned in-frame upstream of the S/MAR region is placed under control of a constitutive promoter sequence, such as a CMV constitutive promoter.

FIG. 2 depicts a schematic overview of an embodiment of the transgenic system according to the present invention, whereby the said telomere length maintenance gene rTERT and the S/MAR region in the regulation region (2) are controlled by a constitutive P$_{CMV}$ promoter sequence. Therefore the S/MAR region will be continuously transcribed in-frame with rTERT and present in the host cell, hereby maintaining the presence of said transgene. The said transgene is independent of the presence of said inducing agent and therefore cannot be eliminated from the host cell. The transgene as depicted in FIG. 2 can for instance be of particular use for the production by human B lymphocytes of therapeutic monoclonal antibodies. In presence of the inducing agent, the said G1-specific tumour suppressor shRNA sequence in the regulation region of said transgene is transcribed and prevents expression of the corresponding tumour suppressor: transgenic cells enter the cell cycle and multiply, but do not secrete monoclonal antibody, a situation reminiscent of the lymphoblast stage in vivo. Upon retrieval of the inducing agent, B lymphocytes exit the cell cycle, accumulate somewhere in G1 where they remain quiescent and synthesize monoclonal antibody, a situation which reflects the in vivo plasma stage of this type of cells. Whether the inducing agent is present of absent from the growth medium, the rTERT-S/MAR region in said transgene is permanently transcribed ensuring the stability of the said transgenic cell. Generally, in order to immortalize antibody-producing B lymphocytes, these B cells are fused with an actively growing myeloma which does not produce antibodies on itself in order to form hybrid cell lines or hybridomas. By use of the transgene according to the current invention, the formation of these hybrid cell lines is not required, as introduction of said transgene according to the method provided by the current invention will readily immortalize the B lymphocytes.

Example 3

Figure 3:
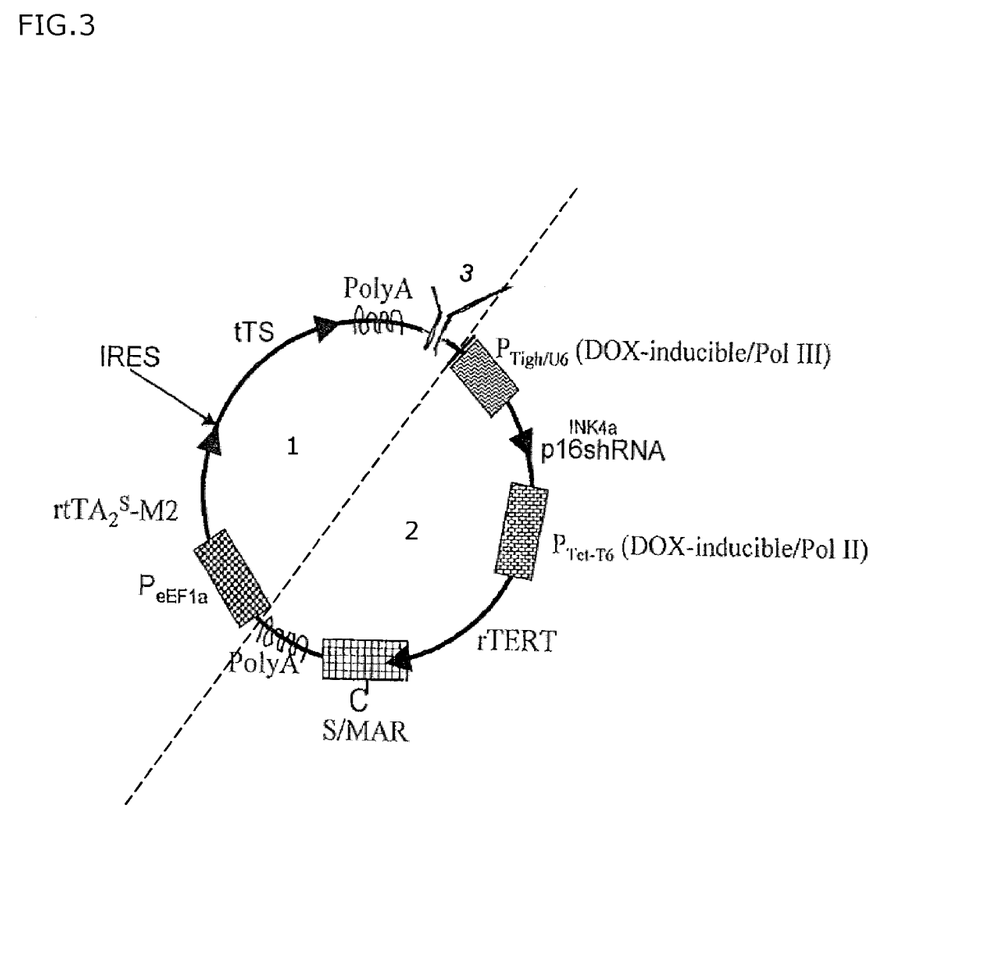
FIG. 3 depicts a schematic overview of another exemplary embodiment of the transgenic system according to the present invention, containing only one transgene, whereby the said transgene is provided with a prokaryotic origin of replication and an antibiotic-independent selection system surrounded by Flp-recombinase sensitive F sites to support transgene replication. shRNA, TERT and S/MAR sequences may be placed under control of doxycycline-inducible promoters.

FIG. 3 depicts a schematic overview of another exemplary embodiment of the transgenic system according to the present invention, whereby the transgene of the transgenic system is provided with a prokaryotic region, in order to support amplification in prokaryotes. As production of minicircles is usually cumbersome and labour-intensive, this can be overcome by inserting a bacterial origin of replication into the said transgene, together with a non-antibiotic selection mechanism (3) (STABY™ Technology, Bacterial host strain E. coli Cys21 expressing ccdB poison gene and temperature-inducible Flp recombinase activity; Szpirer and Milinkovitch, 2005, Biotechniques 38: 775-781; WO02066657, WO9958652, Broll et al., 2010, J. Mol. Biol. 395: 950-965). Hence, this said transgene is able to replicate in bacteria for amplification purpose from which it can be obtained without antibiotic selection. The presence of the S/MAR element, inducibly or constitutively controlled, ensures the replication of the said transgene in the eukaryotic host cell, without integration in the genome of said host cell.

Example 4

Figure 4:
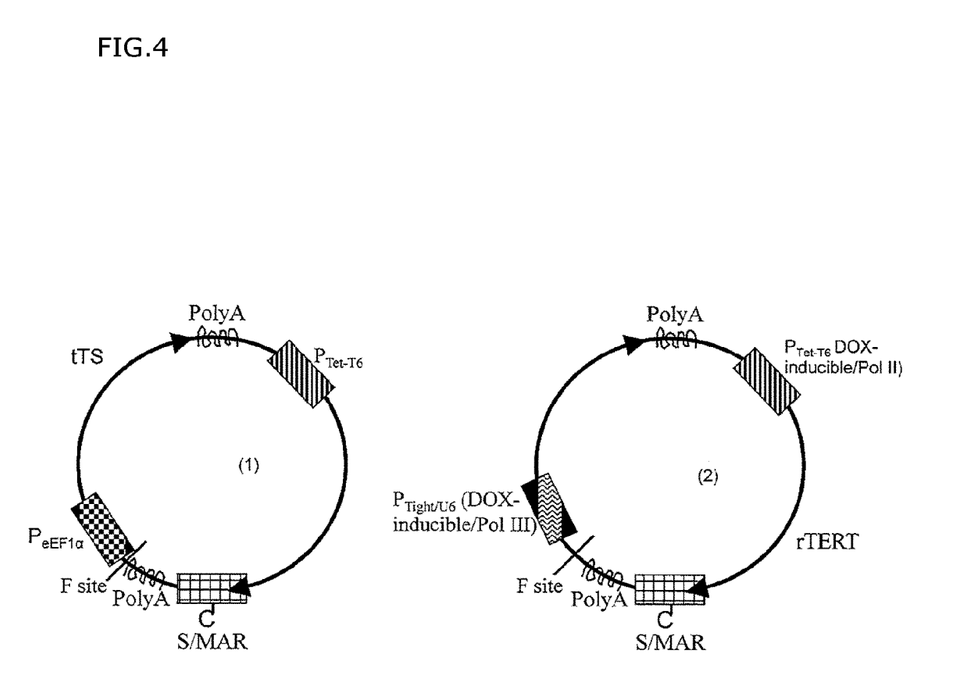

To reduce the overall size of said unique transgene depicted in FIG. 1 and increase accordingly the transgene's stability, FIG. 4 depicts an exemplary embodiment of the transgenic system according to the current invention by distributing the genes of said transgene of FIG. 1 between two transgenes whereby one said transgene contains the genes of the control region (1) and the second said transgene the genes of the regulation region (2). For said transgene containing the genes of the control region (1) to be eliminated in absence of doxycycline, the S/MAR1 element ought to be linked downstream in frame with the transcriptional transactivator rtTA$^s$2-M2 placed under control of said $P_{TET-T6}$ doxycycline-inducible promoter. The regulation region comprises a telomere length homeostasis gene, such as TERT, and an shRNA directed against a G1-tumour suppressor mRNA (see Table 1). An S/MAR2 region is furthermore equally present, placed downstream and in frame of the TERT gene. The expression of the sequences may either be inducible, or constitutive, for instance in the case of the TERT gene operably linked upstream of the S/MAR2 element.

Example 5

Doxycycline—Regulated Reversible Immortalization of Human Keratinocytes
Replication Life Span Determinations Normal proliferating human epidermal keratinocytes from adult foreskin (ref.C 12004) and ready-to-use keratinocyte growth medium 2 (ref. 20211) were both purchased from PromoCell GmbH (Heidelberg, Germany). The cells in 0.5 ml (with or without Doxycycline) were inoculated in triplicate at a cell density of 10 000 cells per cm² in 33 mm diameter tissue culture grade multiwall plates (Becton Dickinson USA) and cultivated at 37° C. in a 5% $CO_2$/air humidified atmosphere cabinet. The growth medium containing 1000 ng doxycycline was changed every other day. When the cells reached 50%-60% confluency, they were enzymatically detached with Invitrogen TrypIE Select™ and passaged Population doublings (PD) per passage was calculated as $\log_2$ number of cells at time of subcultivation/number of cells plated. Replicative life span determination was calculated by plotting the cumulative PD against total time in culture. Cells were considered being immortalized when the cells' life span extended 50 PD beyond that of the untransfected cells.

Immunochemical Analysis of the p16$^{INK4a}$ Tumour Suppressor Protein and Determination of the Telomerase Activity Cell monolayers for control and Doxycycline-containing cultures were rinsed with 2 ml phosphate buffered saline (PBS) and the cells detached with 5 ml Invitrogen's TrypIE Select™ after 4 minutes incubation at 37° C. followed by neutralization of the enzyme with 4 ml of complete growth medium. Following one rinse of the cell pellet (5 min at 2000 rpm) with 5 ml PBS, the cells were lysed in 20 ml Tris-HCl buffer (pH 7.3) containing 2% sodium dodecyl sulphate and 1 mM dithiothreitol, their protein content being determined (for instance by the Bradford method). Twenty to eighty μg of proteins were separated by sodium dodecyl sulphate polyacrylamide gel electrophoresis using a polyacrylamide concentration of 14% (w/v).

Proteins were electrotransferred with a Mini-ProteinII Trans Blot apparatus to Hybond P PVDF membrane and probed with mouse anti-human p16$^{INK4a}$ monoclonal antibody generated to the —COOH terminus of the tumour suppressor protein (Santa Cruz Biotechnology-Santa Cruz, Calif., USA). The antibody was used at a 1/1000 dilution in blocking buffer (4% milk powder and 0.2% Tween 20 in PBS) at 4° C. overnight.

The blots were then incubated with horseradish peroxidase-conjugated goat anti-mouse secondary antibody followed by enhanced chemiluminescence detection, the results being visualized by X-ray film. Telomerase activity was detected using PCR-based Telomerase Repeat Amplification Protocol (TRAP) assay (Kim and Wu, Nucleic Acids Res., 1997, 25: 2595-2597).

Transfection

Fifty thousand keratinocytes in 200 μl complete growth medium (CGM) were inoculated per well of a 6-well culture plate and allowed to grow overnight (18-24 h) until 50-60% confluency. Butyrate was then added to reach a final concentration (Broil, S. et al., 2010, 395: 950-965) and the cells incubated during 36 h. Butyrate was then withdrawn by medium exchange and the cells washed twice to remove all traces of the histone deacetylase inhibitor. The cells were transfected with Roche X-Treme 9 DNA transfection according to the manufacturer's protocol. Four hours after transfection, an equivalent volume of growth medium was exchanged by CGM (10% fetal calf serum) containing 1000 ng doxycycline and exchanged under these conditions every other day.

Example 6

Doxycyline—Regulated Immortalization of Human Pancreatic Beta Islet Cells
Replicative Life Span Determinations Islets of Langerhans were prepared from a human adult brain dead pancreas donor in accord with Belgian regulations and with the local institutional ethical committee. Processing of the tissue was as described by Lukowiak (Lukowiak, B. et al. J Histochem Cytochem 49 (2001) 519-528) with Invitrogens TrypIE Select™ replacing trypsin during the dissociation step used to prepare the isolated islet cell suspension.

Staining with Newport Green (lipophilic diacetate ester form) at 25 µM was achieved after a period of 90 min. in F10 growth medium without calcium, containing 2.8 mM glucose. Sorting was performed using the BD Facscan. Replicative life span determinations were performed in the same way as those described for human keratinocytes (Example 5).

Immunochemical Analysis of the p16 Tumour Suppressor Protein and Determination of the Telomerase Activity.

The immunochemical analysis was performed in the same way as described for human keratinocytes (Example 5) using the same mouse anti-human $p16^{INK4a}$ monoclonal antibody as used with human keratinocytes (Example 5).

Transfection

Transfection of human pancreatic beta islet cells was performed essentially in the same way as described for human keratinocytes (Example 5).

Example 7

Doxycyline—Regulated Immortalization of Human Hepatocytes

Replicative Life Span Determinations

Normal human hepatocytes isolated from the normal liver of a single donor (ref C 12850) and ready-to-use hepatocyte growth medium (ref C 25010) with or without Doxycyline at 1000 ng/ml, were both purchased from PromoCell GmbH (Heidelberg, Germany).

Replicative life span determinations were performed in the same way as those described for human keratinocytes (Example 5).

Immunochemical Analysis of the $p15^{INK4b}$ Tumour Suppressor Protein and Determination of the Telomerase Activity.

The immunochemical analysis was performed in the same way as described for human keratinocytes (Example 5), using mouse anti-human $p15^{INK4a}$ monoclonal antibody instead of $p16^{INK4a}$ to probe the hepatocyte protein lysate for the presence of the $p15^{INK4b}$ tumour suppressor protein.

Transfection

Transfection of human hepatocytes was performed essentially in the same way as described for human keratinocytes (Example 5).

Example 8

Doxycyline—Regulated Immortalization of Human Osteoblasts

Replicative Life Span Determinations

Normal proliferating human osteoblasts from femoral bone tissue from the knee or the hip region (ref C 12706) obtained from PromoCell GmbH (Heidelberg, Germany) are cultivated in MEM (Life Technologies Inc., Grand Island, N-Y) supplemented with 10% FCS, 200 mM glutamine and antibiotics (Penicilline and Streptomycine at 500 mM each) with or without Doxycyline at 1000 ng/ml. Medium was changed every other day, care being taken to subcultivate the culture before reaching influence.

Replicative life span determinations were performed in the same way as those described for human keratinocytes (Example 5).

Immunochemical Analysis of the $p27^{Kip1}$ Tumour Suppressor Protein and Determination of the Telomerase Activity Following cell detachment performed as described for human keratinocytes (Example 5) the cells were lysed in 50 mM Tris-HCl pH 7.2 containing 120 mM NaCl, 0.5% NP40, 1 mM EDTA, 1 mM dithiothreitol, 1 mM PMSF, Protease inhibitor cocktail (Roche Complete, EDTA-free, ref. 11873580001) 1 tablet/50 ml lysis buffer. Following an incubation of 15 minutes on ice and a centrifugation (10 min at 2000 g) the supernatant total protein being qualified by Bradford assay, the proteins are separated by sodium dodecyl sulphate polyacrylamide gel electrophoresis as described earlier (Example 5).

Transfection

Transfection of human osteoblasts was performed essentially in the same way as described for human keratinocytes (Example 5).

What is claimed is:

1. A transgenic system for reversibly immortalizing quiescent cells, comprising a non-viral, circular non-integrating transgene, wherein said transgenic system comprises a control region (1) and a regulation region (2), whereby said control region (1) comprises a transcriptional regulation system operably linked to a constitutive promoter sequence and said regulation region (2) comprises:
    a) an RNA interference sequence which prevents translation of a G1-tumour suppressor messenger RNA and which is operably linked downstream of a first inducible promoter sequence;
    b) a single immortalizing gene consisting of a telomere length maintenance gene sequence which is operably linked downstream to a second inducible promoter sequence; and
    c) a Scaffold/Matrix attachment region (S/MAR) element positioned downstream in frame with said telomere length maintenance gene sequence and controlled by the second inducible promoter sequence.

2. The transgenic system according to claim 1, wherein said telomere length maintenance gene sequence encodes for a Telomerase Reverse Transcriptase (TERT) catalytic subunit.

3. The transgenic system according to claim 1, wherein said G1-specific tumour suppressor mRNA to be prevented from translation is selected from the group consisting of $p16^{INK4A}$, $p15^{INK4B}$, $p18^{INK4C}$, $p19^{INK4D}$, $p21^{Cip1}$, $p27^{Kip1}$, and $p57^{Kip2}$.

4. The transgenic system according to claim 1, wherein said transcriptional regulation system is a Tet-induced system and comprises a constitutively expressed transcriptional transactivator and a transcriptional transsilencer.

5. A method to immortalize isolated human quiescent cells from primary cultures, comprising the steps of: a) providing the human quiescent cells from primary cultures; b) introducing the transgenic system according to claim 1 into the human quiescent cells; whereby said transgenic system replicates in phase with the host cell genome without integrating; c) adding an inducing agent to the growth medium of said cells; d) overexpressing the telomere length maintenance gene present in said transgenic system and; e) preventing the translation of a G1-specific tumour-suppressor by a specific mRNA interference sequence present in said transgenic system.

6. The method of claim 5, wherein said inducing agent is doxycycline.

7. The method of claim 5, wherein said prevention of translation of a G1-specific tumour suppressor and said overexpression of the telomere length maintenance gene with the in frame S/MAR region is dependent on the continuous presence of said inducing agent.

8. The method of claim 5, wherein upon removal of said inducing agent from the growth medium, said transgenic system is lost from the host human quiescent cell within a few cell cycles.

9. The method of claim 5, wherein the cells of step (b) are in monolayers and exposed to a histone deacetylase inhibitory enzymatic treatment prior to the introduction of said transgenic system.

10. A transgenic system for reversibly immortalizing quiescent cells, comprising two non-viral, circular non-integrating transgenes wherein said transgenic system comprises a control region (1) and a regulation region (2), wherein said regulation region (2) is present on a first transgene and comprises:
   a) an RNA interference sequence which prevents translation of a G1-tumour suppressor messenger RNA and which is operably linked downstream of a first inducible promoter sequence;
   b) a telomere length maintenance gene sequence which is operably linked downstream to a second inducible promoter sequence; and
   c) a first Scaffold/Matrix Attachment Region (S/MAR) element positioned downstream in frame with said telomere length maintenance gene sequence and controlled by the second inducible promoter sequence;
   and wherein said control region (1) is present on a second transgene and comprises
   d) a transcriptional regulation system operably linked to a constitutive promoter sequence; and
   e) a second Scaffold/Matrix Attachment Region (S/MAR) element.

11. The transgenic system according to claim 10, wherein said second S/MAR element differs from said first S/MAR element.

12. The transgenic system according to claim 10, wherein said G1-specific tumour suppressor mRNA to be prevented from translation is selected from the group consisting of $p16^{INK4A}$, $p15^{INK4B}$, $p18^{INK4C}$, $p19^{INK4D}$, $p21^{Cip1}$, $p27^{Kip1}$, and $p57^{Kip2}$.

13. The transgenic system according to claim 10, wherein said transcriptional regulation system is a Tet-induced system and comprises a constitutively expressed transcriptional transactivator and a transcriptional transsilencer.

* * * * *